United States Patent [19]

Wojtowicz

[11] Patent Number: 4,656,271

[45] Date of Patent: Apr. 7, 1987

[54] PROCESS FOR PRODUCING CYANURIC ACID FROM UREA HYDROHALIDES

[75] Inventor: John A. Wojtowicz, Cheshire, Conn.

[73] Assignee: Olin Corporation, Cheshire, Conn.

[21] Appl. No.: 831,753

[22] Filed: Feb. 21, 1986

[51] Int. Cl.$^4$ .......................................... C07D 251/32
[52] U.S. Cl. .................................................. 544/192
[58] Field of Search ....................................... 544/192

[56] References Cited

FOREIGN PATENT DOCUMENTS 170514 4/1965 U.S.S.R. .
202933 9/1967 U.S.S.R. .

OTHER PUBLICATIONS

Strongin, G. M. and V. I. Smirnov, "Preparation of Urea Hydrochloride," Trudy po khimii i khimicheskoi tekhnologii, No. 2, 1966, pp. 323–325.

Schiltknecht, F. J., "Uber den Reaktionsmechanismus der Pyrolyse von Harnstoff zu Cyanursaure," Prom. Nr. 3403, Zurich, pp. 69–75, 1963.

*Primary Examiner*—John M. Ford
*Attorney, Agent, or Firm*—James B. Haglind; Thomas P. O'Day; William A. Simons

[57] ABSTRACT

A process for producing cyanuric acid which comprises feeding a urea hydrohalide compound to a pyrolysis zone.

The urea hydrohalide compound is pyrolyzed to produce a solid reaction mixture of cyanuric acid and an ammonium halide. The solid reaction mixture is vaporized to remove the ammonium halide to form a gaseous mixture containing ammonia and hydrogen halide which is simultaneously removed from the pyrolysis zone. The cyanuric acid recovered is substantially free of ammonium halide.

The novel process produces high purity cyanuric acid in the absence of liquid effluents while readily recovering the ammonia and hydrogen halide values.

20 Claims, 5 Drawing Figures

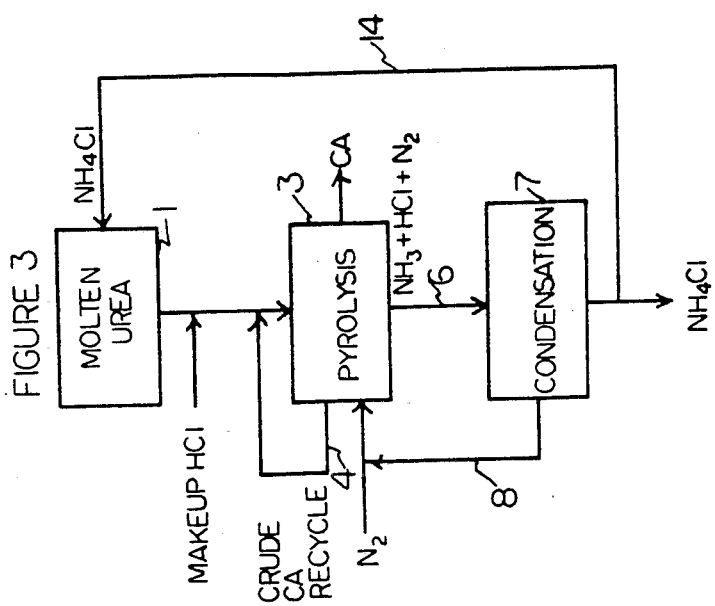
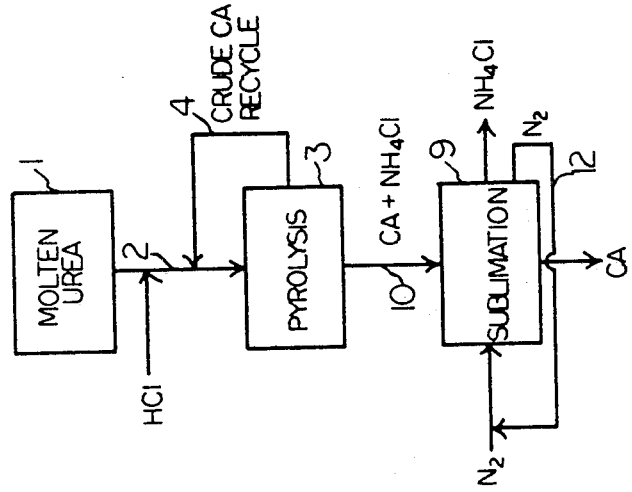
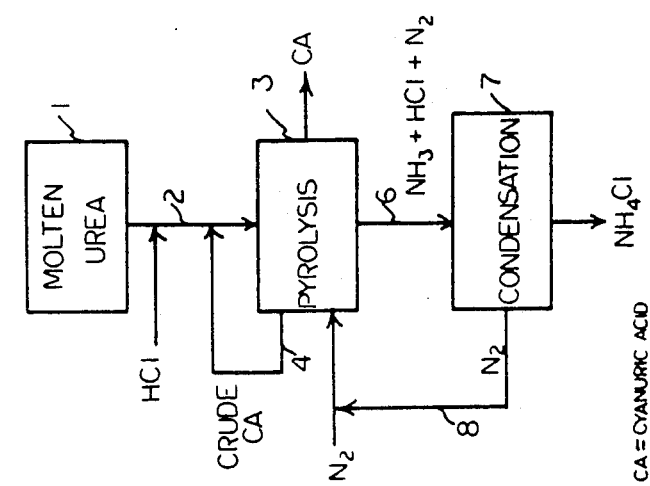

PROCESS FOR PRODUCING CYANURIC ACID FROM UREA HYDROHALIDES

This invention relates to a novel process for producing cyanuric acid by pyrolytic conversion of urea hydrohalide.

It is known that cyanuric acid can be produced by the pyrolysis or urea. This reaction may be expressed by the equation:

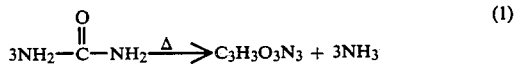

The resulting product, cyanuric acid, which has the empirical formula $C_3H_3O_3H_3$, is generally represented structurally either as:

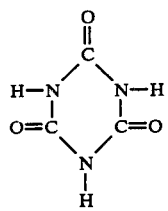

or

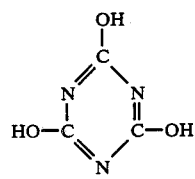

The pyrolysis can be carried out either in a dry state, that is, in the absence of a solvent, such as described in U.S. Pat. No. 2,943,088, issued to R. H. Westfall on June 28, 1960, or in the presence of various inert organic solvents, such as described in the U.S. Pat. No. 2,952,679, issued to Perret on Sept. 18, 1960 (dipropylene glycol); U.S. Pat. No. 3,065,223, issued to Hopkins et al on Nov. 20, 1962 (alkyl sulfones); U.S. Pat. No. 3,117,968, issued to Merkel et al on Jan. 14, 1974 (diphenyl); U.S. Pat. No. 3,164,591, issued to Walles et al on Jan. 5, 1965 (oxazolidinones); U.S. Pat. No. 3,563,987, issued to Berkowitz on Feb. 16, 1971 (sulfolane); U.S. Pat. No. 3,635,968, issued to Goelz et al on Jan. 18, 1972 (N-cyclohexyl pyrrolidone); or U.S. Pat. No. 3,810,891, issued to Lee on May 14, 1974 (glycol ethers).

Unfortunately, the pyrolysis of urea to produce cyanuric acid is not a selective reaction, but rather, a range of products, in addition to cyanuric acid, can be produced. These products may include amino substituted cyanuric acids, commonly referred to as amides of cyanuric acid, namely ammelide, ammeline, and melamine, as well as other undesirable side products, such as ammonium carbamate and other condensation products.

It is also known to form cyanuric acid by the pyrolysis of urea hydrochloride. F. Schiltknecht, in Ueber den Reaktion mechanismus der Pyrolyse von Harnstoff Zu Cyanursaeure, pp. 69–75, Zurich, 1963, describes a pyrolysis method in which urea hydrochloride is heated at temperatures of 220°–240° C. for 2–5 hours to form cyanuric acid and ammonium chloride. The reaction product was washed with water and the cyanuric acid recovered.

Schiltknecht also teaches that ammonium chloride is first sublimed at a temperature of 335° C.

At temperature of 335° C., while ammonium chloride may sublime, considerable amounts of cyanuric acid are also sublimed and poor separation of the reaction products results.

Further, G. M. Strongin and V. I. Smirnov (Tr. Khim. i Khim Tekhnol, 1966, No. 2, 323–325) describe a method for preparing urea hydrochloride by saturating urea with hydrogen chloride and further heating the reaction mixture. At temperatures of 120°–125° C., a urea hydrochloride having a melting point of 130° C. is formed while a low-melting urea hydrochloride (mp. 50° C.) is formed at temperatures below 90° C.

The urea hydrochloride formed is then heated by Strongin et al (USSR Inventors Certificate No. 170,514, Feb. 25, 1965) at temperatures in the range of 220°–260° C. to prepare a cake of cyanuric acid. The cake is subsequently cooled and ground and then leached with rinsing water at −10° C. and the cyanuric acid recovered.

Both of the above processes result in the formation of liquid effluents containing ammonium chloride and cyanuric acid. These effluents require further treatment or disposal.

In addition, these processes result in the loss of ammonia, hydrogen chloride and ammonium chloride values as these compounds cannot be readily recovered from the liquid effluents.

There is, therefore, need for a commercial process for the production of cyanuric acid in which high purity cyanuric acid is produced in good yields and is readily recovered from the reaction mixture without generating liquid effluents.

Surprisingly, it has now been discovered that effective separation of the two products of the pyrolysis reaction can be readily obtained without forming liquid effluents.

It is an object of the present invention to provide a process for producing high assay cyanuric acid which can be readily recovered from the reaction mixture.

Another object of the invention is to provide a process for producing cyanuric acid substantially free of cyanuric acid amides.

An additional object of the present invention is to provide a continuous process for producing cyanuric acid having reduced requirements for raw materials.

A further object of the present invention is to provide a process for producing cyanuric acid free of the co-production of liquid effluents.

These and other objects of the invention are accomplished in a process for producing cyanuric acid which comprises:

(a) feeding a urea hydrohalide compound to a pyrolysis zone, (b) pyrolyzing the urea hydrohalide compound to produce a solid reaction mixture of cyanuric acid and an ammonium halide, (c) vaporizing the ammonium halide from the solid reaction mixture to form a gaseous mixture containing ammonia and a hydrogen halide while simultaneously removing the gaseous mixture from the pyrolysis zone, and (d) recovering cyanuric acid substantially free of the ammonium halide.

FIG. 1 presents a flow sheet of one embodiment of the process of the present invention in which anhydrous hydrogen chloride is a reactant and solid ammonium chloride is recovered.

FIG. 2 illustrates an alternate embodiment of the process of the present invention.

FIG. 3 represents an additional embodiment of the process of the present invention in which a portion of the solid ammonium chloride recovered is recycled.

Figure 5:
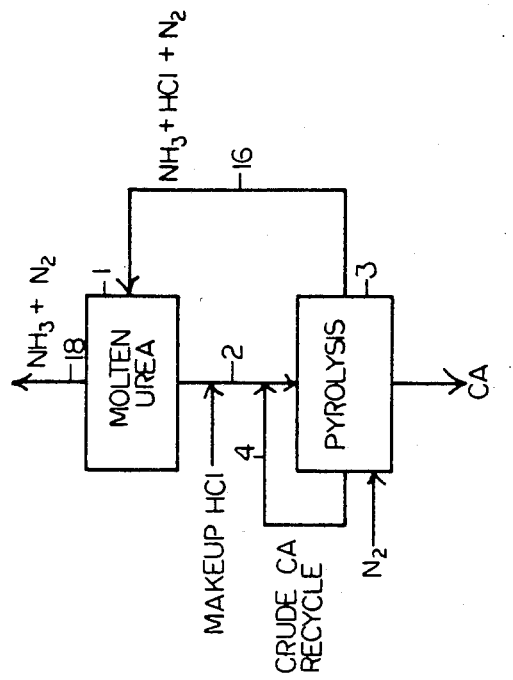
FIG. 5 illustrates another embodiment of the present invention in which the gaseous mixture from the pyrolysis reaction is recycled.

More in detail, in the embodiment of the process of the present invention shown in the FIGURES, molten urea is employed as one of the reactants. The second reactant is an anhydrous hydrogen halide. Suitable hydrogen halides include hydrogen bromide, hydrogen chloride, hydrogen fluoride, and hydrogen iodide, with hydrogen chloride and hydrogen bromide being preferred. For the sake of simplifying the disclosure, the process of the present invention will be described using anhydrous hydrogen chloride as the hydrogen halide, as illustrated in FIGS. 1-5.

As depicted in FIG. 1, molten urea is conveyed from vessel 1 through line 2 to pyrolysis kiln 3. Also added to line 2 is anhydrous hydrogen chloride, and following the initial start-up period, crude cyanuric acid from pyrolysis vessel 3 is recycled to line 2. Urea hydrochloride is formed during the reaction of the urea with HCl and is pyrolyzed in pyrolysis kiln 3 to produce cyanuric acid and a gaseous mixture of ammonia and hydrogen chloride. A carrier gas, such as nitrogen, is fed to pyrolysis kiln 3 to convey the gaseous mixture to condensation vessel 7. Solid ammonium chloride is formed and separated from the nitrogen-containing carrier gas, which is recycled to pyrolysis kiln 3.

In the embodiment of the novel process of the present invention illustrated in FIG. 2, the reaction mixture of cyanuric acid and ammonium chloride from pyrolysis kiln 3 is conveyed to sublimation vessel 9 and solid ammonium chloride recovered from the cyanuric acid product.

In an alternate embodiment of the process of FIG. 1, the process of FIG. 3 recycles a portion of the solid ammonium chloride recovered from condensation vessel 7 to be admixed with molten urea in vessel 1. This process, after the startup period, requires only make-up amounts of anhydrous HCl to be added.

In the novel process of the present invention, the urea, in solid or molten form, readily absorbs the anhydrous HCl to produce urea hydrochloride in a reaction which can be represented by the following equation:

$$NH_2CONH_2 + HCl \rightarrow NH_2CONH_2 \cdot HCl \qquad (2)$$

While in the embodiments illustrated in FIGS. 1-5, the urea hydrochloride is produced in situ and conveyed directly to the pyrolysis kiln, if desired, urea hydrochloride can be isolated by known means for subsequent use in the process or for sale.

Cyanuric acid is produced by the pyrolysis of solid urea hydrochloride at a temperature above about 150° C., for example, from about 150° C. to about 300° C. and preferably from about 230° to about 270° C. The pyrolysis is represented by the following equation:

$$3\ NH_2CONH_2 \cdot HCl \rightarrow C_3H_3N_3O_3 + 3NH_3 + 3HCl \qquad (3)$$

The pyrolysis is continued until the conversion of the urea hydrochloride is substantially complete. When the process is operated continuously, suitable pyrolysis times are those of less than about 200 minutes, and preferably less than about 100 minutes, and more preferably from about 30 to about 60 minutes.

The pyrolysis reaction, in another embodiment, is run under pressure to reduce any dissociation of urea hydrochloride to urea and HCl and thus minimize the formation of cyanuric acid amides such as ammelide and ammeline. Suitable pressures, for example, are those in the range of from about 1.5 to about 5 atmospheres at the pyrolysis temperatures discussed above.

In an alternate embodiment, hydrogen chloride gas is continuously fed to the reaction mixture during pyrolysis to enhance the purity of the cyanuric acid product.

A highly pure cyanuric acid product is recovered from the reaction mixture by removing the gaseous mixture of ammonia and hydrogen chloride from the pyrolysis zone at about the rate of formation to permit the vaporization of additional ammonium chloride from the reaction mixture. Suitable methods of removing the gaseous mixture include the use of vacuum means or feeding a carrier gas to the pyrolysis zone. Examples of carrier gases which can be employed are nitrogen, air, or mixtures thereof.

The gaseous mixture removed from the pyrolysis zone is contacted with a condensing means to produce solid ammonium chloride, and where employed, recover the carrier gas. The formation of solid NH$_4$Cl readily takes place upon contact of the gaseous mixture with a surface at ambient temperature or temperatures up to about 150° C. While surfaces at lower temperatures may be used, they are not required.

Figure 4:
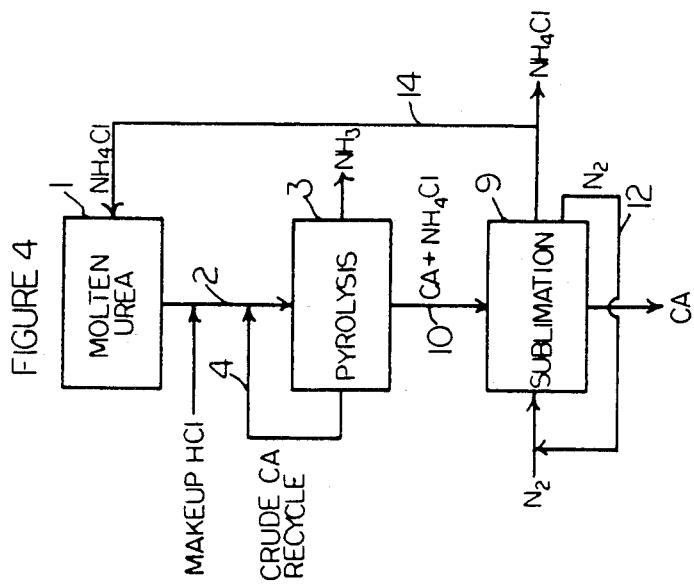
FIG. 4 depicts a further embodiment of the process of the present invention.

In an alternate embodiment, as illustrated in FIGS. 2 and 4, the solid reaction mixture of cyanuric acid and ammonium chloride formed in the pyrolysis zone, is conveyed to a sublimation zone. Ammonium chloride is vaporized at temperatures up to about 300° C., and preferably temperatures in the range of from about 150° C. to about 290° C., and more preferably at from about 225° C. to about 270° C., at atmospheric pressure.

Alternately, the sublimation may be carried out at lower temperatures under vacuum conditions.

Condensation of the gaseous mixture formed in the sublimation zone to produce solid NH$_4$Cl takes place in the manner described above.

Solid ammonium chloride produced by the process of the present invention may be sold commercially. A portion of the solid ammonium chloride recovered may be recycled to the process to partially supply the requirements for the hydrogen chloride used in the process, as illustrated by the embodiments shown in FIGS. 3 and 4.

In one embodiment, as illustrated by FIG. 5, the gaseous mixture is returned directly to be admixed with urea. This recycling step also permits a substantial reduction in the requirements for hydrogen chloride.

The cyanuric acid produced by the novel process of the present invention is of high assay, substantially free of ammonium halide, and contains only minimal amounts of amides such as ammelide and ammeline. In addition, the product yields are excellent and the cyanuric acid is readily recovered without requiring costly purification procedures. The process of the present invention is carried out without the production of aqueous effluents such as acidic solutions of ammonium chloride which require treatment and disposal. Further, the process provides the ready recovery of ammonium chloride values.

While the novel process of the present invention may be operated batchwise, it is preferably operated on a continuous basis.

To further elucidate the novel process of the invention without being limited thereby, the following examples are presented. All parts and percentages are by weight unless otherwise specified.

EXAMPLE 1

Gaseous hydrogen chloride was continuously added to a reaction vessel containing powdered urea. The reaction temperature was maintained in the range of 60°–85° C. until equivalent molar amounts of hydrogen chloride gas and urea had been reacted. The liquid reaction mixture was slowly heated until the temperature of the reaction mixture reached about 150° C., when the reaction exothermed to about 250° C. Heating of the reaction mixture was continued for about 30 additional minutes. The cyanuric acid product was slurried in water, filtered, washed with water and dried. A 93 percent yield of cyanuric acid was obtained having a purity of 98.7 percent.

EXAMPLE 2

The procedure of EXAMPLE 1 was repeated exactly with the exception that following the addition of the stoichiometric amount of hydrogen chloride gas, a slow addition of HCl was continued throughout the reaction period. The filtrate recovered from the filtration step was evaporated to dryness and analyzed for cyanuric acid. The combined yield was 92 percent of cyanuric acid having a purity of 100 percent.

EXAMPLE 3

Twenty grams of a mixture of cyanuric acid (10 g) and $NH_4Cl$ (10 g) were added to a U-shaped reactor having an air condenser attached. The reactor, flushed with $N_2$ gas, was heated in an oil bath. Ammonium chloride sublimed from the reaction mixture was collected in the air cooled condenser maintained at room temperature. Periodically, the ammonium chloride was removed from the condenser, weighed and analyzed. The sublimation reaction data is shown in TABLE 1 below.

TABLE 1

| Sublimation Time (hrs) | $N_2$ CC/Min | Oil Bath Temp. °C. | $NH_4Cl$ g | CA |
|---|---|---|---|---|
| 4 | 20 | 250 | 2.02 | |
| 7 | 40 | 255–270 | 4.31 | ND |
| 2.5 | 40 | 260–270 | 1.26 | |
| 3 | 40–50 | 270 | 2.56 | ND |
| | | TOTAL | 10.15 | |

The residue after removal of $NH_4Cl$ weighed 9.8 g assayed 99.7 percent cyanuric acid and contained 0.1 percent $NH_4Cl$. A substantially complete removal of $NH_4Cl$ was accomplished.

EXAMPLE 4

A reaction mixture produced by the process of EXAMPLE 1 was placed in a vacuum sublimation vessel and heated on an oil bath at 150° C. Ammonium chloride crystals, which condensed on a cold finger, were collected and dissolved in water. The solution was titrated with $AgNO_3$ and found to contain 85.6 percent of the theoretical amount of $NH_4Cl$.

What is claimed is:

1. A process for producing cyanuric acid which comprises:
    (a) feeding a urea hydrohalide compound to a pyrolysis zone,
    (b) pyrolyzing the urea hydrohalide compound to produce a solid reaction mixture of cyanuric acid and an ammonium halide,
    (c) vaporizing the ammonium halide from the solid reaction mixture to form a gaseous mixture containing ammonia and a hydrogen halide while simultaneously removing the gaseous mixture from the pyrolysis zone, and
    (d) recovering cyanuric acid substantially free of the ammonium halide.

2. The process of claim 1 in which the ammonium halide is selected from the group consisting of ammonium bromide, ammonium chloride, ammonium fluoride and ammonium iodide.

3. The process of claim 1 in which the ammonium halide is ammonium chloride or ammonium bromide.

4. The process of claim 3 in which the gaseous mixture is removed by employing a vacuum.

5. The process of claim 4 in which the ammonium halide is ammonium chloride.

6. The process of claim 3 in which the gaseous mixture is removed from the pyrolysis zone by feeding a carrier gas to admix with said gaseous mixture.

7. The process of claim 6 in which the gaseous mixture removed from the pyrolysis zone is admixed with molten urea in a mixing vessel.

8. The process of claim 7 in which said carrier gas is selected from the group consisting of hydrogen chloride, nitrogen, air, and mixtures thereof.

9. The process of claim 2 in which said gaseous mixture is conveyed to a condensing zone to condense solid ammonium chloride from the carrier gas.

10. A process for producing cyanuric acid which comprises:
    (a) feeding a urea hydrohalide compound to a pyrolysis zone,
    (b) pyrolyzing the urea hydrohalide to produce a solid reaction mixture of cyanuric acid and an ammonium halide,
    (c) conveying the solid reaction mixture to a sublimation zone,
    (d) vaporizing the ammonium halide to form a gaseous mixture containing ammonium halide vapors,
    (e) condensing the gaseous mixture to produce solid ammonium halide, and
    (f) recovering cyanuric acid substantially free of the ammonium halide.

11. The process of claim 10 in which said gaseous mixture is condensed at from about ambient temperature to about 150° C.

12. The process of claim 11 in which a carrier gas is fed to the sublimation zone.

13. The process of claim 12 in which the urea hydrohalide compound is urea hydrochloride and the ammonium halide is ammonium chloride.

14. The process of claim 13 in which a portion of the cyanuric acid recovered is admixed with the urea hydrochloride prior to feeding the urea hydrochloride to the pyrolysis zone.

15. The process of claim 13 in which a portion of the ammonium chloride is admixed with molten urea and anhydrous hydrogen chloride to produce urea hydrochloride.

16. The process of claim 13 in which the vaporization of the ammonium chloride is at a temperature of from about 150° C. to about 290° C.

17. The process of claim 16 in which the carrier gas fed to the sublimation zone is selected from the group consisting of nitrogen, air, and mixtures thereof.

18. The process of claim 1 in which the pyrolyzing is continuous at a pyrolysis temperature of from about 150° C. to about 300° C. and a pyrolysis time of less than about 200 minutes.

19. The process of claim 1 in which pyrolyzing the urea hydrochloride is operated at a pressure of from about 1.5 to about 5 atmospheres.

20. The process of claim 13 in which pyrolyzing the urea hydrochloride is conducted at a temperature of from about 230° C. to about 270° C. and a pyrolysis time of from about 30 to about 60 minutes.

* * * * *